United States Patent [19]

Levy et al.

[11] 4,081,402

[45] Mar. 28, 1978

[54] HYDROPHILIC ABSORBENTS

[75] Inventors: Didya D. Levy, Brooklyn, N.Y.; Samuel H. Ronel, Princeton, N.J.

[73] Assignee: National Patent Development Corporation, New York, N.Y.

[21] Appl. No.: 551,016

[22] Filed: Feb. 19, 1975

Related U.S. Application Data

[63] Continuation-in-part of Ser. No. 384,230, Jul. 31, 1973, abandoned.

[51] Int. Cl.$^2$ .................. B01J 31/02; A61K 31/74
[52] U.S. Cl. ................................. 252/428; 252/426; 252/430; 424/78
[58] Field of Search .............. 252/427, 428, 477 R, 252/426, 430

[56] References Cited

U.S. PATENT DOCUMENTS

| 3,442,819 | 5/1969 | Herbert | 252/428 |
| 3,538,020 | 11/1970 | Heskett et al. | 252/428 |
| 3,746,655 | 7/1973 | Urbanic | 252/428 |
| 3,813,347 | 5/1974 | Hayes | 252/428 |

Primary Examiner—Sam Rosen
Attorney, Agent, or Firm—Cushman, Darby & Cushman

[57] ABSTRACT

Products are prepared of solid hydrogel matrixes having entrapped therein high-surface area sorbent materials, preferably activated carbon. The entrapped absorbent has an effective surface area no greater than about 1% of the actual surface area of the sorbent material, e.g., activated carbon per se, preferably not over 0.001%. The products are particularly useful in radioimmunoassay for antigens.

17 Claims, 9 Drawing Figures

Fig. 1.

SEPARATION BY CONVENTIONAL MEDIA

1. SERUM SAMPLE CONTAINING EXTRACTED (I.E LIBERATED) THYROXINE. (O).

2. SAMPLE AFTER ADDING A FIXED QUANTITY OF RADIOACTIVE THYROXINE (●) AND A FIXED QUANTITY OF THYROXINE ANTIBODY ( ⊔ )

3. BOTH LABELLED AND NON-LABELLED THYROXINE BIND THE THYROXINE ANTIBODY ( ⊓ ).

4. A SOLUTION OF DEXTRAN-COATED ACTIVATED CHARCOAL (DCC) IS ADDED TO THE TUBE, THE DCC SORBS THE UNBOUND THYROXINE AND IS THEN SPUN DOWN IN A CENTRIFUGE LEAVING BEHIND THE ANTIBODY-ANTIGEN COMPLEX IN THE SUPERNATANT.

5. THE SUPERNATANT IS THEN DECANTED INTO A SECOND TUBE AND COUNTED SEPARATELY IN AN APPROPRIATE RADIOISOTOPE.

Fig. 2.

SEPARATION BY FASTAB

1. SERUM SAMPLE CONTAINING EXTRACTED (I.E., LIBERATED) THYROXINE. (○)
2. SAMPLE AFTER ADDING A FIXED QUANTITY OF RADIOACTIVE THYROXINE (●), A FIXED QUANTITY OF THYROXINE ANTIBODY (⌐), AND A FASTAB.
3. BOTH LABELLED AND NON-LABELLED THYROXINE BIND THYROXINE ANTIBODY WHILE THE UNBOUND THYROXINE IS SORBED BY THE FASTAB.
4. THE SOLUTION IS POURED OFF AND THE FASTAB IS COUNTED.

HYDROPHILIC ABSORBENTS

This application is a continuation-in-part of copending application Ser. No. 384,230 entitled Coatings of WaterInsoluble Solid Hydrophilic Polymer by S. H. Ronel and D. D. Levy, filed July 31, 1973 and now abandoned.

The present invention relates to novel products comprising hydrogels having dispersed therein a sorbent as defined hereinafter, to novel methods for preparing such products, and to novel uses involving such products.

Radioimmunoassay (RIA) is a technique for measuring very small quantities of biologically active compounds that exist in physiological fluids such as serum, urine, and spinal fluid. These compounds exist in quantities as low as one picogram per liter of solution, i.e., $10^{-12}$ grams/liter. Conventional chemical techniques for measuring these quantities are inadequate hence the use of a radioactive tracer in the assay procedure. By their very nature, radioactive isotopes can be detected at very low concentrations by suitable counting instruments.

In general terms, RIA fundamentally involves a large molecule called an antibody (MW $\geq$ 150,000) forming a loose chemical bond with a single, specific type of molecule called an antigen. The reaction is basically an immune-specific one, meaning that the antibody will react with only a single type of antigen to the exclusion of all other materials that exist in the solution. Further, the antibody will react with that particular antigen with no regard to the possibility that it may be radioactive. The antigens that are most frequently assayed, are hormones (either protein or steriod), drugs, vitamins, or almost any other metabolite that could be found in a physiological solution.

For illustrative purposes, consider a well-known prior art technique used to assay for total serum thyroxine in vitro. Thyroxine is a non-protein hormone secreted by the thyroid gland and is basic to many metabolic and growth functions. Most of this hormone is bound to serum proteins and is unavailable for metabolic purposes. In order to assess thyroid function, a serum sample is first treated to liberate all thyroxine, i.e., all of the thyroxine in the serum sample is rendered unbound and thus available for binding to thyroxine antibody. At this point, a fixed amount of radioactive thyroxine and a fixed amount of thyroxine antibody is added to the tube. Both the radioactive and serum thyroxine will compete for a limited number of binding sites on the antibody. If, in the extreme, there is little or no serum thyroxine, then only the radioactive thyroxine will bind to the antibody and form a radioactive antibody-antigen complex. If, in the opposite extreme, there is a large excess of serum thyroxine, egs., 99% of all the thyroxine in the tube is non-radioactive, then in this example, about 99% of all antibody-antigen complexes formed will be non-radioactive. As the percent of serum thyroxine in solution increases, the percent of radiolabeled complex decreases. Each test tube contains the same total amount of tracer even though a certain percent of that tracer is now complexed to the antibody. In order to make the test meaningful, that percent of radioactive tracer which has been bound to antibody must be removed from solution and counted separately. Once the complex has been removed from solution, its radioactivity can be measured. The greater the radioactivity of the complex, the lower the amount of serum thyroxine.

One prior method for resolving solutions containing both bound antigen and free antigen involves the addition of a fluid and watery suspension of activated charcoal having a very thin coating of dextran. This watery suspension of charcoal sorbs primarily the relatively low molecular weight antigen. Once this is done, the charcoal is spun down in a centrifuge and the supernatant, which ideally contains only the antibody-antigen complex, is poured off and counted separately. The count is then compared to a calibration curve and the equivalent amount of serum thyroxine is read directly from the calibration graph.

Conventional radioimmunoassays are performed, for example, on serum solutions and require the precise additions of reagents, primarily antiserum and radiolabeled antigen, and a medium, such as a water suspension of dextran-coated charcoal, to separate the bound antigen from the free fraction. The protocol for such RIA determinations involves several laborious and exacting steps which require precision and careful control by the operator.

For example, in a prior art method of determining the metabolically active quantity of thyroxine in a serum sample, i.e., the free thyroxine concentration, two separate and distinct determinations must be made: The first procedure requires liberating all bound thyroxine from their thyroxine binding proteins by an, e.g., alcohol extraction technique, and then determining the total thyroxine concentration (T4). The second procedure requires a determination of the bound thyroxine component (T3). These two values, i.e., T4 and T3, will then together yield an index of the free thyroxine component.

Current techniques for directly measuring the free thyroxine component have not proven commercially attractive. Reasons for this stem from the fact that the free component represents less than 1% of the total serum thyroxine and technical problems exist in resolving the free component from the bound component.

In employing a conventional centrifugal procedure, the carbon particles are spun down and the supernatant containing the antibody-antigen complex is poured off. These steps take time. However, prior to the centrifugation step, the activated carbon being such a strong adsorbent, can cause the disassociation of the antibody-antigen complex (known in the art as "antigen stripping"), with the result that the disassociated antigen is also adsorbed by the activated charcoal.

The disadvantages of RIA prior art techniques are overcome by employing a solid hydrogel matrix having dispersed therein a microporous, relatively high-surface area sorbent material, e.g., activated carbon. While activated carbon will rub off leaving a black smudge, e.g., when touched or rubbed with a finger, no observable black smudge rubs off when the novel hydrogel matrix-activated carbon products are rubbed with a finger.

The novel solid hydrogel matrix-sorbent product can exist in a variety of regular or irregular shapes. Desirably, it can be in the form of a tablet, cylindrical or rectangular rod, disc, sphere, a coating, e.g., within a cylinder (or other shaped article) made for example of glass or inert plastic.

The novel hydrogel matrix-sorbent products are highly effective in the resolution of solutions containing molecules of widely varying molecular weight, e.g., in free antigen separation and in other radioimmunoassay determinations, in dialysis applications, in the detoxification of liquid streams, etc. Molecules of molecular weight of about 10,000 and above are generally not absorbed by the novel products.

The invention will be understood best in connection with the drawings wherein.

The novel articles of manufacture obviate many limitations attending conventional sorbents in antigen separation and analysis by:

Providing a barrier to prevent adsorption of the relatively high molecular weight molecule, e.g., antibody-antigen complex;

Negating the need for precise pipetting of the sorbent;

Negating the need for precise control of the time the sorbent is in contact with the test medium;

Negating the need for contrifugation as a pelletizing technique for removing the sorbent from the test medium.

For example, the article of this invention can be used in a method for quickly and inexpensively directly determining the free thyroxine component on samples of unextracted serum without the need for antiserum (antibody).

The method of the invention in such use has the advantages over existing methods as follows:

Only one test is required to determine the free thyroxine serum concentration as opposed to the two tests currently required to make a comparable determination;

The determination is made directly on serum without the need to first extract the serum proteins by ethanol precipitation;

Although radiolabeled thyroxine is required for the determination, just as it is in conventional tests, no antibody is required; and No centrifugations are required by standard protocols.

The Novel articles comprise hydrogels having dispersed therein a particulate sorbent hereinafter defined. Such articles have a high affinity for relatively low molecular weight compounds. When the novel article is employed in various RIA techniques, said article has the ability to resolve mixtures comprised of components of widely different molecular weights, e.g., antibody-antigen mixtures. For example, once the antigen has been sorbed in the product of the invention, it is extremely difficult to be washed out in an aqueous medium. In contrast, known polyacrylamide gels used as separation media suffer from the disadvantage of allowing the antigen to be washed out much more readily.

The novel product, when cut to shape - a disc for example - can be deposited in a test medium containing both bound and free antigen. The novel hydrogel-carbon product will sorb the free antigen leaving behind the bound antigen in the medium. The hydrogel-carbon product is then removed from the test medium leaving behind a clinically significant test solution enriched in complexed or bound antigen.

The presence of the activated carbon or other sorbent dispersed in the hydrogen matrix prevents the thyroxine or other antigen from eluting from the novel product.

The separation method for resolving, for example, mixtures containing bound and free thyroxine, comprises the steps of:

a. Obtaining a serum sample and placing the same in an appropriate test tube.
b. Adding a precise, known amount of radiolabeled thyroxine (antigen).
c. Adding the novel product, e.g., FASTAB, to the serum-antigen mixture.
d. Allowing the novel product to reside in said mixture for a specified period of time.
e. Removing said novel product from the test tube.
f. Separately counting both the test tube and/or the novel product in an appropriate radioisotope detector.

The novel products (comprising a hydrogel matrix and particulate sorbent dispersed therein are characterized by the following properties: (i) solid, (ii) insoluble in deionized water and common organic vehicles, e.g., lower alkanols, (iii) normally shape-retaining in the dehydrated state as well as in the fully hydrated state, i.e., that state which is attained when the novel product is immersed in deionized water and is in osmotic equilibrium therewith thereby reaching its final dimensions, (iv) water-swellable to the extent that it possesses a deionized water-uptake value of from 200% to 2000%, preferably from 250% to 1000%, and preferably still 450% ± 150%, based on the weight of the dehydrated product, (v) a partition coefficient of at least 2, (vi) an average molecular weight diffusion limitation of about 10,000 Daltons, and (vii) a gross external surface area no greater than about one percent of the total surface area of total microporous sorbent dispersed therein, desirably no greater than about 0.01 percent, and preferably no greater than about 0.0001 percent. For example, the gross external surface area of a cube of novel product having each edge equal to 12 mm. would be 1728 $mm^3$.

The products of the invention include the dehydrated products as well as the partially hydrated and fully hydrated form. Also within the scope of the invention are hydrophilic polymers containing a particulate sorbent dispersed therein and which are partially or completely swollen with a water-miscible organic diluent, e.g., ethylene glycol, glycerol, etc.

By the term "partition coefficient ($k$) of the novel product" is meant the ratio of the equilibrium concentration of antigen in a unit volume of said novel product relative to the equilibrium concentration of the same antigen in a like unit of solution, said novel product residing in an equilibrium state with said solution (the antigen being, for example, thyroxine). On the other hand, by the term "partition coefficient ($k$) of the hydrogel per se" is meant the ratio of the equilibrium concentration of antigen in a unit volume of said hydrogel relative to the equilibrium concentration of the same antigen in a like unit of solution, said hydrogen residing in an equilibrium state with said solution. By the term "average molecular weight diffusion limitation" is meant the ability to resolve solutions containing components of different molecular weights such that components having an average molecular weight below 10,000 Daltons would readily diffuse into the novel product while essentially excluding those components whose average molecular weight is greater than 10,000. The term "Dalton" represents a unit of molecular weight.

Illustrative subclasses of such water-insoluble, hydrophilic polymers include the polymers of hydroxyalkyl 2-alkenoates and of hydroxy lower alkoxy lower alkyl 2-alkenoates; the partially hydrolyzed polymers of a vinyl ester of a carboxylic acid, e.g., partially hydrolyzed vinyl acetate homopolymers and copolymers; the polymers of vinyl alkyl ether such as the homopolymers and copolymers of vinyl methyl ether and of vinyl ethyl ether; the polymers of vinyl heterocyclics including those which are partially crosslinked such as the homopolymers and copolymers of vinylpyridine, of N-vinylpyrrolidone, and of N-vinyl-4-methyl-2-oxazolidinone; the partially crosslinked polymers of alkylene oxides, e.g., of poly(ethylene oxide) and of poly(oxyethyleneoxypropylene); the polymers of alkenamides such as the partially crosslinked homopolymers and copolymers of acrylamide, of methacrylamide, of N-lower alkyl acrylamides, of N-lower alkyl methacrylamides, of N,N-di-lower alkyl acrylamides, and of N,N-dilower alkyl methacrylamides, e.g., polymers of N-methylacrylamide, of N,N-dimethylacrylamide, of N-methylmethacrylamide, of N,N-dimethylmethacrylamide, of N-ethylacrylamide, of N-isopropylacrylamide, of N-butylacrylamide, of N,N-diethylacrylamide, of N-propylacrylamide; and others.

The hydrogels or hydrophilic polymers, especially the 2-hydroxyethyl methacrylate polymers, which are especially desirable are those which have average molecular weights (as applied in solution and prior to curing for the 2-hydroxyalkyl 2-alkenoate polymers) greater than about 40,000 and upwards to a few million, e.g., 3 million, preferably from about 50,000 to 1,000,000 and more preferably from about 75,000 to 500,000.

The hydrophilic polymers which are particularly preferred in the practice of the invention are the polymers of hydroxyalkyl acrylate and of hydroxyalkyl methacrylate as exemplified by a 2-hydroxyethyl acrylate or a 2-hydroxyethyl methacrylate polymer. There can be used, as indicated previously, other hydrophilic polymers such as polymers of hydroxyalkyl acrylates, of hydroxyalkyl methacrylates, of hydroxy lower alkoxy lower alkyl acrylates, and of hydroxy lower alkoxy lower alkyl methacrylates such as polymers of hydroxypropyl acrylate, of hydroxyethyl acrylate, of hydroxypropyl methacrylate, of hydroxyethoxyethyl acrylate, of hydroxyethoxyethyl methacrylate, of hydroxypropoxypropyl acrylate, of hydroxypropoxypropyl methacrylate, of triethylene glycol monoacrylate, and of triethylene glycol monomethacrylate.

The preferred monomers for preparing the hydrophilic polymers are hydroxyalkyl acrylates and hydroxyalkyl methacrylates having 2–3 carbon atoms in the hydroxyalkyl moiety, most preferably 2-hydroxyethyl methacrylate.

The hydroxyalkyl acrylate or hydroxyalkyl methacrylate can also be replaced in whole or in part by vinylpyrrolidone, acrylamide, N,N-dimethylacrylamide, N-N-diethylacrylamide, N-ethylacrylamide, methacrylamide, N-propylacrylamide, N-isopropylmethacrylamide, N-methylacrylamide, N-methylmethacrylamide, N-methylolacrylamide and N-methylolmethacrylamide, N-(2-hydroxyethyl)acrylamide, N-(2-hydroxyethyl)methacrylamide. Since these monomers usually form water soluble polymers, they require the presence of sufficient cross-linking agent to render the resulting polymeric products water insoluble.

Other ethylenically unsaturated monomers can be used as comonomers in conjunction with the above monomers to prepare the hydrophilic polymeric matrices. They include monomers such as the alkenenitriles, e.g., acrylonitrile, methacrylonitrile; the alkenyl alkanoates, e.g., vinyl acetate; the alkyl 2-alkenoates, e.g., methyl acrylate, ethyl acrylate, butyl acrylate, 2-ethylhexyl acrylate, methyl methacrylate, and butyl methacrylate; the alkoxyalkyl 2-alkenoates, e.g., methoxyethyl acrylate, methoxyethyl methacrylate, ethoxyethyl acrylate, ethoxyethyl methacrylate, propoxyethyl acrylate, butoxyethyl methacrylate, methoxypropyl acrylate, and ethoxypropyl methacrylate. Such illustrated comonomers should not be used in an amount sufficient to impair the hydrophilic nature of the resulting polymer product. Other vinyl comonomers, in small amounts, can be used, e.g., acrylic acid, methacrylic acid, aminoethyl methacrylate, dimethylaminoethyl methacrylate, and the like. To "tailor-make" the hydrogel matrix of choice, it may be desirable to employ 3, 4, and even 5 or more monomers in the polymerization reaction, with the proviso that the resulting polymeric product falls within the characterizations set forth herein with respect to the hydrogel matrix used in the preparation of the novel products. The concentration of the monomers (excluding the cross-linking agent) used in the polymerization reaction can vary over the entire range, providing, of course, that the resulting polymeric product has the characteristics set forth in this specification.

To make the final product insoluble in water or organic solvents, it is eventually cross-linked. This is done by sparingly cross-linking the polymeric products. Preferably, the cross-linking agent is added in an amount not exceeding 10%, most preferably not over 2.0%, and still more preferably between 0.1% and 1%, although from 0.05 to 15% or even 20% of cross-linking agents can be used. Cross-linking renders the otherwise organic solvent soluble or water soluble polymers insoluble, although the cross-linking agents should not be used in an amount sufficient to impair the hydrophilic properties of the final product.

Typical examples of cross-linking agents include ethylene glycol diacrylate, ethylene glycol dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinylbenzene, divinyltoluene, diallyl tartrate, allyl malate, divinyl tartrate, triallyl melamine, N,N'-methylene bisacrylamide, divinyl ether, diallyl monoethylene glycol citrate, ethylene glycol, vinyl allyl citrate, allyl vinyl maleate, ethylene glycol diester of itaconic acid, divinyl sulfone, polyester of maleic anhydride with triethylene glycol, and divinyl citraconate. Of course toxic cross-linking agents should not be used in therapeutic applications.

The hydrogel matrices, i.e., the hydrogel or hydrophilic polymer per se, which are suitably employed in the practice of the invention are: (i) solid, (ii) insoluble in deionized water and common organic vehicles, e.g., lower alkanols such as methanol, ethanol, etc., (iii) normally shape-retaining in the dehydrated state as well as in the fully hydrated state, i.e., that state which is attained when the hydrogel per se is immersed in deionized water and is in osmotic equilibrium therewith thereby reaching its final dimensions, (iv) water swellable to the extent that it possesses a deionized water-uptake value of from 60% to 4,000%, desirably from 500% to 3,000%, and preferably from 1000% to 2500%, based on the weight of the dehydrated hydrogel, (v) a partition coefficient of at least 2, and (vi) an average molecular weight diffusion limitation of about 10,000 Daltons.

In a broad aspect, the novel products comprise a hydrogel as hereinbefore defined and a particulate microporous sorbent dispersed therein. In the practice of particularly suitable embodiments of the invention, the sorbent employed is characterized by a relatively high surface area, e.g., upwards to about a few thousand square meters/gram, and is homogeneously dispersed throughout the hydrogel matrix.

Particular suitable sorbents per se which are dispersed within the solid, water-insoluble, water-swellable hydrophilic polymer include a wide variety of inorganic and organic substrates having the following characteristics: (i) pore volume of from 0.3 to 1.5 cc/gm, usually at least 0.5 cc/gm, preferably from 0.6 to 1.2 cc/gm; (ii) pore size of which at least 50 percent of the pores have a diameter of less than 1 micron, more preferably less than 150 A and usually from 5 A to 100 A; most preferably at least 80 percent of the pores have a diameter of from 10 A to 100 A; and (iii) surface area of 5 square meters/gram to 4000 square meters/gram, and desirably from 100 to 1500 square meters/gram.

When the sorbent is activated carbon, the surface area of the activated carbon is desirably about 500 to almost 1500 m²/gram, preferably from about 900 to 1200 m²/gm, more preferably about 950 to 1150 m²/gm. The pore volume is preferably about 0.6 to 1.2 cc/gm.

Illustrative of the sorbents which are suitable in the practice of the invention include a wide variety of activated carbons from various sources such as lignite, wood charcoal, peat, petroleum, coconut shells, bituminous coal, petroleum, etc.

Other sorbents which can be used include the ion exchange resins as illustrated hereinafter.

Among the anion exchange resins, there can be used cross-linked styrene resins containing quaternary ammonium groups, e.g., quaternized chloromethylated styrene-divinyl benzene resins, e.g., where the quaternizing group in $-N(CH_3)_3+$ as in Amberlite IRA 400, as well as Amberlite CG 400 (a quaternarized styrene-divinyl benzene copolymer which in the basic form has the grouping $-CH_2N(CH_3)OH$ attached to the aromatic nucleus).

Weak base anion exchange resins can also be employed such as cross-linked aminated chloromethylated styrene resins, e.g., trimethylaminomethyl styrene-divinyl benzene copolymer. (There can also be used phenol-formaldehyde-polyalkylene polyamine resins, e.g., wherein the polyethylene polyamine is triethylene tetramine, tetraethylene pentamine, or diethylene triamine).

Weakly acidic ion exchange resins can also be used, e.g., Amberlite 8-IRA, a cross-linked poly(methacrylic acid) as well as cross-linked polyacrylic acid.

Strongly acidic cation exchange resins can be used such as cross-linked sulfonated styrene resins such as sulfonated styrene-divinyl benzene resins such as Dowex 50, Amberlite IR-120, Amberlite CG-120-Ar, and Zeo Carb 225. There can also be used sulfonated phenol-formaldehyde resins.

Amphoteric and mixed cation and anion exchange resins can also be used.

Typical ion exchange resins which are suitable are disclosed in Encyclopedia of Polymer Science and Technology, Vol. 7, pages 692–742 (1967), the entire disclosure of which is incorporated by reference. Thus, any of the commercial ion exchange resins set forth on pages 696–698 can be used. There also can be used anion and cation exchange resins such as any of those disclosed in the following patents. The entire disclosures of the following 15 United States Patents and 8 British Patents are hereby incorporated by reference.

U.S. Pat. No. 2,340,111 (to D'Alelio), e.g., acrylic acid ethylene dimethacrylate copolymer.

U.S. Pat. No. 2,341,907 (to Cheetham), e.g., diphenylol dimethyl methane-dimethylamine-formaldehyde resin, U.S. Pat. No. 2,366,007 (to D'Alelio), e.g., sulfonated styrene-divinylbenzene copolymer, U.S. Pat. No. 2,469,683 (to Dudley), e.g., epichlorohydrintetraethylene pentamine resin, U.S. Pat. No. 2,500,149 (to Boyer), e.g., sulfonated styrenedivinyl benzene copolymer, U.S. Pat. No. 2,591,573 (to McBurney), e.g., the quaternary ammonium reaction product of chloromethylated styrene-divinyl benzene copolymer with trimethyl amine.

U.S. Pat. No. 2,591,574 (to McBurney), e.g., the insoluble resinous reaction product of chloromethylated styrene-divinyl benzene copolymer with dimethyl amine or with tetraethylene pentamine, U.S. Pat. No. 2,632,001 (to McMaster), e.g., the chlorinated methylstyrene-divinyl benzene copolymer quaternarized with trimethyl amine, U.S. Pat. No. 2,675,359 (to Schneider), e.g., triethylenetramineethyl acrylate-divinyl benzene insoluble anion-exchange resin, U.S. Pat. No. 2,764,562 (to Drake), e.g., the methylene phosphonic acid derivative of styrene-divinyl benzene copolymer, U.S. Pat. No. 2,837,488 (to Ferns), e.g., the alpha-hydroxyphosphonic acid containing resin prepared from methyl vinyl ketone-divinyl benzene copolymer treated with phosphorous trichloride and then hydrolyzed, U.S. Pat. No. 2,911,378 (to Bregman), e.g., the product prepared by reacting the copolymer of styrene-divinyl benzene with phosphorus trichloride, oxidizing to form the phosphonate and then hydrolyzing, U.S. Pat. No. 3,122,514 (to Abrams), e.g., Example 1, U.S. Pat. No. 3,132,112 (to Bartolmeo), e.g., the polymer from ammonia and epichlorhydrin, U.S. Pat. No. 3,137,659 (to Kekish), e.g., the anion exchange resin from ammonia and epichlorhydrin, British Pat. No. 726,918, e.g., the phosphonic acid cation exchange resin of Example 1 thereof, British Pat. No. 757,398, e.g., the condensation product of mono (o-hydroxyphenyl) phosphate with formaldehyde, British Pat. No. 777,248, e.g., the partially hydrolyzed triallyl phosphate polymer, British Pat. No. 778,104, e.g., hydrolyzed acrylonitriledivinyl benzene-methyl methacrylate copolymer, British Pat. No. 781,400, e.g., acrylic acid-divinyl benzene-methacrylic acid copolymer prepared by hydrolyzing the copolymer of methyl acrylate-divinyl benzene and methacrylic acid anhydride, British Pat. No. 748,238, e.g., the product of Example 3 thereof, British Pat. No. 829,696, e.g., the anion exchange resin prepared in Example 1 thereof, and British Pat. No. 849,122, e.g., the cation exchange resin of Example 3 thereof.

The ion exchange resins are preferably of the cross-linked sulfonated styrene or quaternary ammonium styrene type.

Still other sorbents include alumina, the activated aluminas, sodium alumina silicate, very finely particulate activated silica, zirconium phosphate, zirconium magnesium phosphate, zirconium phosphomolybdate, zirconium silicate, zirconium vanadate, zirconium cobalt phosphate, zirconium manganese phosphate, zirconium calcium phosphate, zirconium aluminate, zirconium oxide, magnesium oxide, dialdehyde starch, oxidized starch, sodium calcium hydrate, molecular sieves such as Linde 3A, 4A, 4AXH, 5A, 10X and b 13X, the the like. Mixture of sorbents can be used, if desired.

The molecular sieves for example include zeolitic-metalloalumino silicates, e.g., sodium aluminosilicate and calcium sodium aluminosilicate, desirably having pores of substantially between about 7 A and about 13 A. The molecular sieves also include the crystalline synthetic sodium aluminum silicates, calcium aluminum silicates, calcium sodium aluminum silicates, sodium magnesium aluminum silicates, lithium sodium aluminum silicates, sodium potassium aluminum silicate, barium aluminum silicate, lithium aluminum silicate including for example the molecular sieves disclosed in U.S. Pat. No. 2,882,243 and U.S. Pat. No. 2,882,244.

The novel products can contain 0.01 to about 50 weight percent of the sorbent, preferably activated carbon, based on the weight of the polymer per se. The sorbent is preferably 1 to 30%, more preferably about 10 to 25% by weight of the dehydrated hydrogel or hydrophilic polymer.

Other components can also be contained in the hydrogelsorbent product or be attached by physical or chemical means to the surface of such product. For example, such adsorbed or absorbed components lend additional features or advantages to the novel product in that, for example, complexed mixtures can be resolved by immuno-specific reactions, hydrolytic reactions, and other types of chemical reactions. For instance, a hydrogel containing particulate activated charcoal and urease dispersed therein is effective in resolving urea-containing solutions in that urease will hydrolyze the metabolite urea and the products of this hydrolytic reaction will be adsorbed by the dispersed activated charcoal. Without the dispersed urease, the hydrogel-activated charcoal product would be less effective in resolving such urea-containing solutions.

The novel products, e.g., FASTAB, are prepared by a novel process involving the following sequential steps;

1. The polymerizable monomers are added to the reaction vessel, e.g., HEMA and cross-linking agent.

2. Then the initiator, e.g., t-butyl peroctoate, is added thereto.

3. Then the accelerator, e.g., redox system, is added thereto. (Steps 2 and 3 can be interchanged or the initiator and accelerator can be added simultaneously or steps 1, 2 and 3 can be carried out simultaneously or step 2 and/or 3 can precede step 1.)

4. Then there is added water plus a sorbent slurry to the resulting mixture, e.g., an activated carbon slurry in water, (or simply an aqueous activated carbon slurry can be added without separate water addition). The mixture is preferably maintained under stirring at ambient temperatures, e.g, 20° C., or slightly elevated temperatures, desirably in the absence of oxygen, e.g., under a nitrogen blanket.

5. Since the polymerization is quite rapid and exothermic, the resulting prepolymer product while in a homogeneous and fluid or pourable state is poured into a mold, e.g., a mold formed between two glass plates. The polymerization reaction is continued until substantially complete, at mildly elevated temperatures, e.g., 40° – 70° C. The resulting molded product can be post cured for a period ranging from several minutes to several hours, e.g., 10 minutes to 4 hours, at elevated temperatures, e.g., 50° – 150° C. After this, there is obtained from the mold the novel product, e.g., FASTAB, in the shape of the mold. As a practical matter, the mold is of sufficient size to form relatively large sheets. From such sheets the desired shape of the ultimate product can be formed, e.g., disc, cube, etc.

Illustrative free radical initiators include t-butyl peroctoate, isopropyl percarbonate, benzoyl peroxide, methyl ethyl ketone, cumene hydroperoxide, dicumyl peroxide, or there can be employed high energy radiation such as cobalt 60 irradiation. The initiator can be used in conventional amounts as can the redox system. A redox system comprises a reducing agent and an oxidizing agent. Illustrative oxidizing agents include ammonium persulfate, sodium persulfate, potassium persulfate, hydrogen peroxide, etc. Illustrative reducing agents include sodium metabisulfite, ascorbic acid, ferrous ions, e.g., ferrous sulfate, cupric ions, e.g., cupric sulfate, sodium thiosulfate, hydrazine, hydroxylamine, $Ti^{+3}$ salts, sodium sulfide, resorcinol, etc.

It should be noted that if the activated carbon or other sorbent is added prematurely, i.e., if it is added before or with the monomers, there results an incomplete polymerization, or at best low yields of a relatively poor polymer product, i.e., hydrogel plus sorbent.

If the accelerator is not added to the reaction vessel the polymerization reaction is too slow, thus causing the activated carbon, or other sorbent, to settle and form a dense carbon (sorbent) layer in that section in the resulting "polymeric" product.

The products of the present invention are completely different from watery carbon slurries such as the dextran-coated carbon slurries in U.S. Pat. No. 3,592,888 (to Wolf).

As stated above, the novel products are suitable in radioimmunoassay procedures for the following: peptide hormones such as Insulin, Growth Hormone, ACTH (adrenocorticotropic hormone), Parathyroid Hormone, TSH (thyroid stimulating hormone), LH (leutinizing hormone), Vasopressen, Proinsulin, Secretin, Angiotensin, Oxytocin, Bradykinin, FSH (follicle stimulating hormone), Gastrin, Calcitonin, non-hormonal substances such as Digoxin, Digitoxin, Morphine, cAMP (cyclic adenosine monophosphate), Fructose, Rheumatoid Factor, Folic Acid, non-peptidal hormones such as Aldosterone, Testosterone, Dihydrotestosterone, Estradiol, Estrone, Estriol, Prostaglandins, Thyroxine, Triiodothyronine, as well as other metabolites including hormones such as Cortisone, Progesterone, Cortisol, Corticosterone, Progesterone, and 11-Desoxycortisol.

Figure 1:
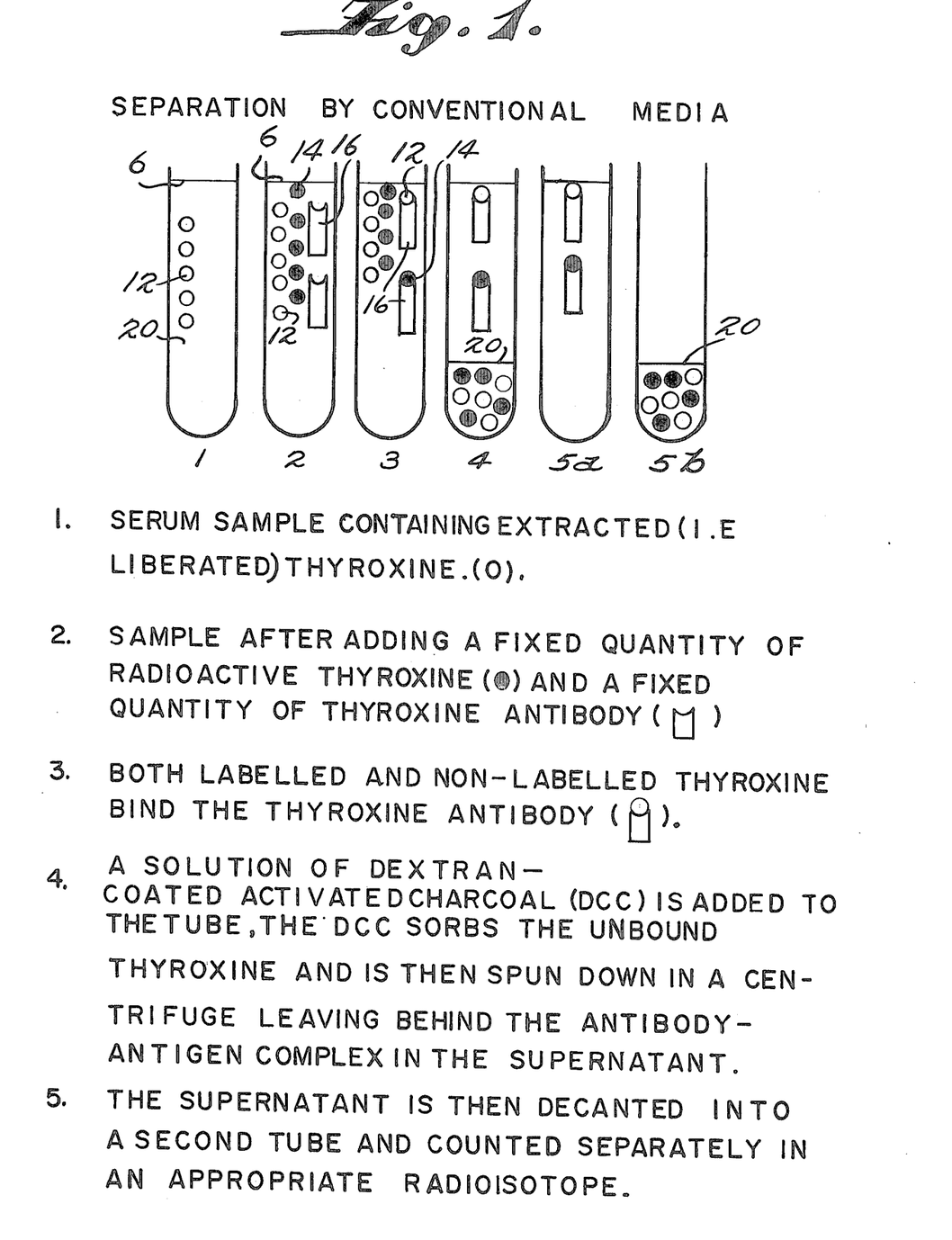
FIG. 1 shows separation of thyroxine by conventional media.

Referring more specifically to FIG. 1 of the drawings, there is illustrated a prior art separation method by the use of conventional media, i.e., a water-suspension of dextran-coated charcoal, wherein in test tube 1 a serum sample 6 is taken containing extracted thyroxine 12. Then as shown in test tube 2, a fixed quantity of radioactive thyroxine 14, e.g., $^{125}$I-Thyroxine, and a fixed quantity of thyroxine antibody 16 is added to said sample. As shown in test tube 3, both labeled (i.e., $^{125}$I-Thyroxine) and non-labeled thyroxine bind the thyroxine antibody. Next as shown in test tube 4, an aqueous suspension of dextran-coated activated charcoal 20 is added to the test tube. The carbon sorbs the unbound thyroxine and is then spun down in a centrifuge leaving behind the antibody-thyroxine complex in the supernatant liquid. The supernatant liquid is then decanted into a second test tube 5a and counted separately in an appropriate radioisotope detector while, as shown in test tube 5b, the unbound thyroxine is sorbed by the dextran-coated charcoal remaining after pouring off the supernatant liquid.

Figure 2:
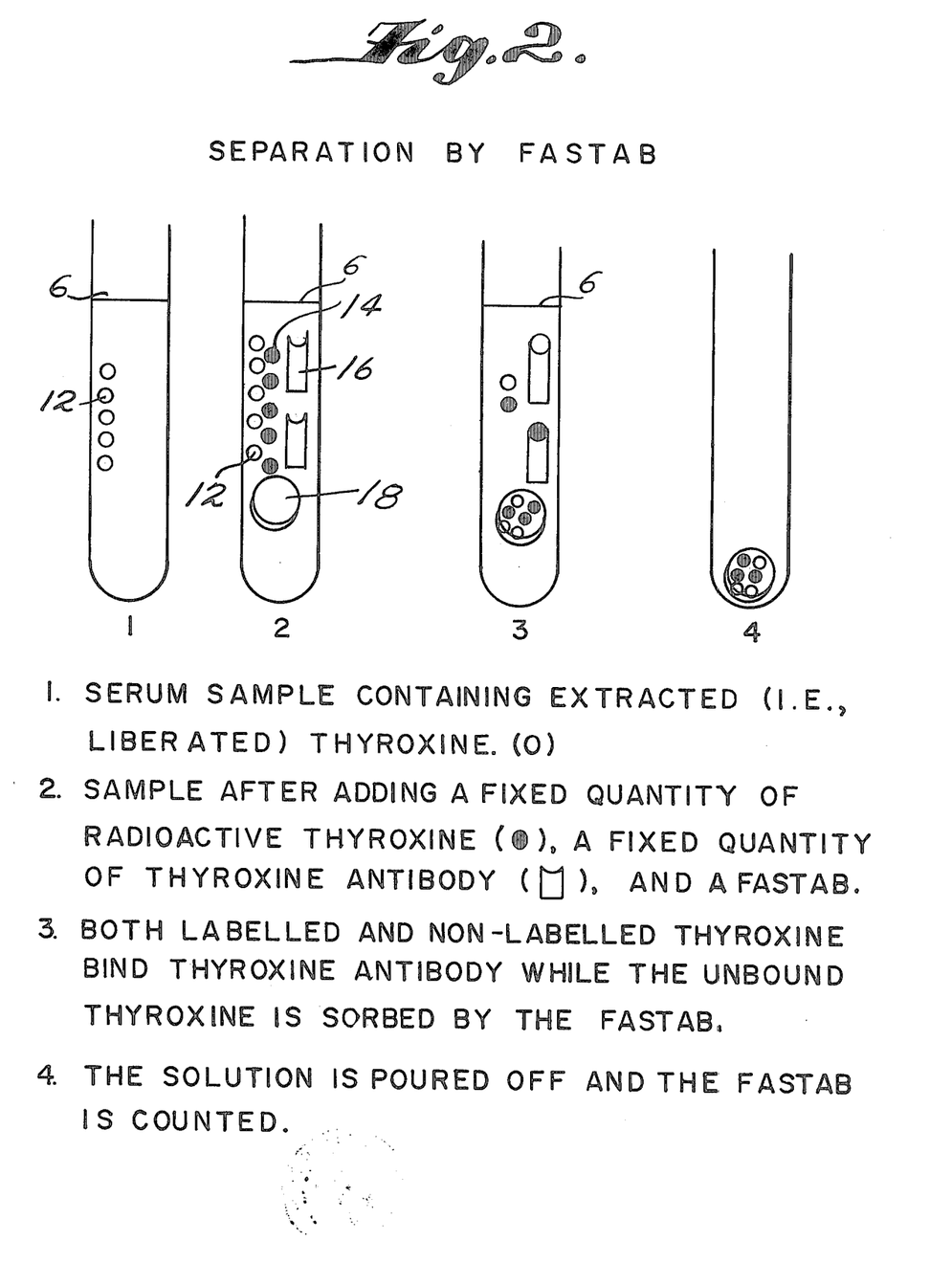
FIG. 2 shows separation of thyroxine according to the invention using FASTAB, i.e., 44% 2-hydroxyethyl methacrylate/55.7% dimethacrylamide/0.3% ethylene glycol dimethacrylate hydrophilic polymer containing 20% by weight of dispersed activated charcoal, based on the weight of said polymer.

FIG. 2 shows the separation by FASTAB, 20 weight percent of particulate activated charcoal dispersed in a hydrogel of 44 weight percent HEMA/55.7 weight percent dimethylacrylate/0.3 weight percent ethylene glycol dimethacrylate. Test tube 1 contains a serum sample 6 containing extracted thyroxine 12 (the same as in FIG. 1). Then as shown in test tube 2 a fixed quantity of the radioactive thyroxine 14 and a fixed quantity of thyroxine antibody 16 as well as a FASTAB 18 is added to the sample. As shown in test tube 3 both labeled 12 and non-labeled 14 thyroxine bind the thyroxine antibody 16 while some of the unbound thyroxine 12 and 14 is sorbed by the FASTAB 18. Then as shown in test tube 4 the solution is poured off and the FASTAB is counted.

The advantages of using the novel products, e.g., FASTAB, include:

1. No pipetting of a separating medium (e.g., dextran-coated activated carbon, polyethylene glycol, etc.), is required.

The novel product is a solid tablet that is dropped into the assay tube together with the serum sample, thyroxine antibody and $^{125}$I thyroxine.

2. Tracer sorption by the novel product is significantly less time-sensitive than sorption by either the prior art dextran-coated activated carbon or anion exchange resins.

3. The removal of the novel product (containing unbound antigen) from the assay tube does not require a centrifugation step. At the end of the incubation period the supernatant liquid in the assay tube is merely decanted, the novel product easily recovered, and then counted in a suitable radioisotope detector.

4. Such RIA determinations require less technical personnel, less equipment, and less time to accomplish the desired end than is required by prior art techniques.

5. The incubation and separation procedures are accomplished in one step. The supernatant does not have to be transferred to another tube; it is simply discarded.

6. It is amenable to completely automated RIA instrumentation.

Unless otherwise indicated, all parts and percentages are by weight.

EXAMPLE 1

A novel HEMA/dimethacrylamide/ethylene glycol dimethacrylate polymer having particulate activated carbon dispersed therein is prepared as follows:

| | |
|---|---|
| t-Butyl peroctoate | 400 microliters |
| Hydroxyethyl methacrylate (HEMA) | 44 grams |
| Dimethylacrylamide (DM) | 56 grams |
| Ethylene glycol dimethacrylate | 300 microliters |
| Activated charcoal | 20 grams |
| Deionized water | 80 ml |
| ammonium persulfate (in 0.5 ml of deionized water) | 300 mg |
| sodium metabisulfite (in 0.5 ml of deionized water) | 300 mg |

The components are added in the order stated in the discussion supra concerning the preparation of the novel process. Polymerization was carried out in a mold at 40° C. for one hour, followed by heating for 2 hours at 100° C. Then, the resulting polymeric product was hydrated in deionized water at about 5° - 10° C. for 48 hours.

Figure 3:
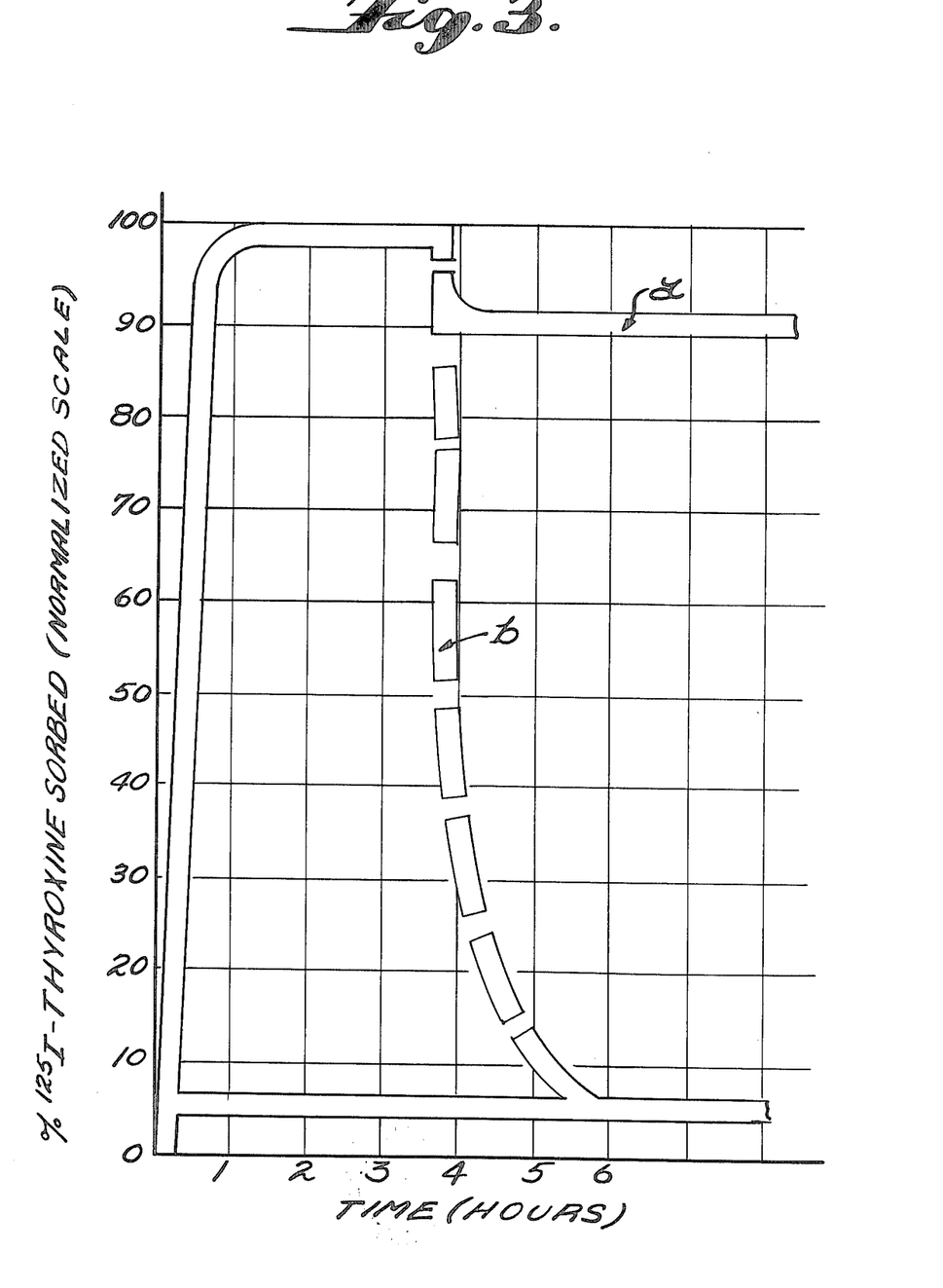
FIG. 3 is a curve showing the absorptive capacity of the novel hydrogel matrix-immobilized activated carbon product for thyroxine.

• In this Example, the mold consisted of two glass plates measuring 12 inches × 12 inches and separated by a gasket approximately 2mm thick. The thickness of the resulting molded sheet when hydrated to equilibrium was approximately 4mm thick. Using a cork borer, 8mm discs, i.e., 8mm diameter × 4mm thick, were punched from the sheet. These hydrated discs are useful in the resolution of solutions containing both bound and free antigen. A curve demonstrating the rate of labeled thyroxine absorption by the novel product prepared in Example 1 and the resistance of contained thyroxine (in said product) to elution is set forth in FIG. 3. Curve (a) illustrates the kinetics of the elution of $^{125}$I-Thyroxine from the novel product. Curve (b) illustrates the kinetics of $^{125}$I-Thyroxine elution from the corresponding hydrogel per se (no sorbent dispersed therein). That is to say, the novel product containing the absorbed thyroxine when completely immersed in deionized water for 48 hours was observed to contain at least 90 percent of the contained thyroxine. By contrast, the hydrogel per se (no dispersed sorbent) which contained absorbed thyroxine when immersed in the same medium under the same conditions was observed to contain less than 40 percent of the contained thyroxine.

Figure 4:
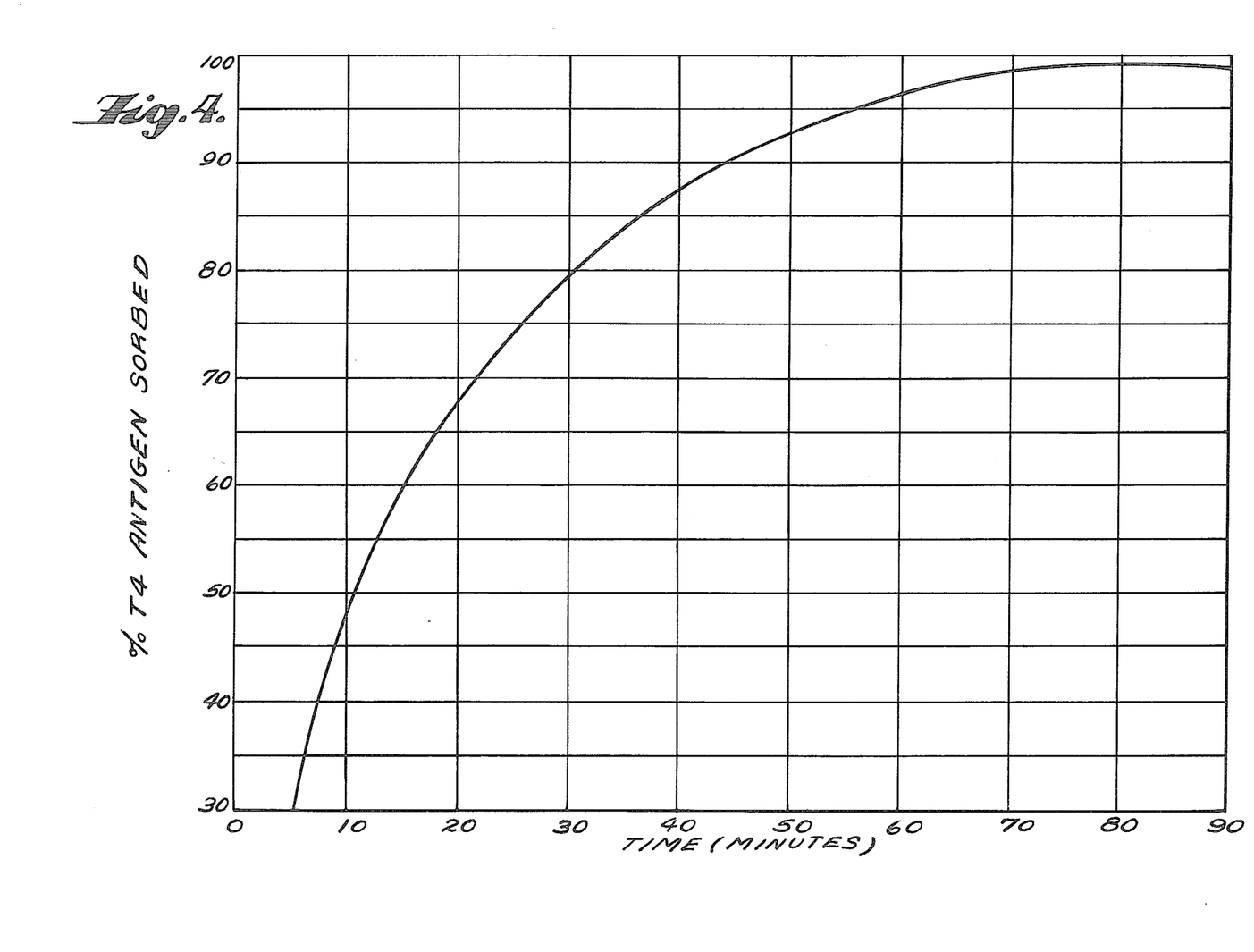
FIG. 4 is a graph depicting the absorption rate for thyroxine in a "zero tube", i.e., a tube containing labelled antigen exclusively.

A clinically significant RIA separation occurs when 40% to 60% of all available antigen has been absorbed from the medium by the activated carbon containing hydrogel. FIG. 4 depicts the absorption rate using the activated carbon containing hydrogel tablets in the so-called "zero tube," i.e., in a tube containing labeled antigen exclusively (in this case $^{125}$I thyroxine). It can be seen that a clinically significant separation occurs in approximately 20 minutes. The curve in FIG. 4 is a plot of the % T-4 antigen uptake (by the novel product prepared by Example 1) vs. time in minutes.

EXAMPLE 2

Figure 5:
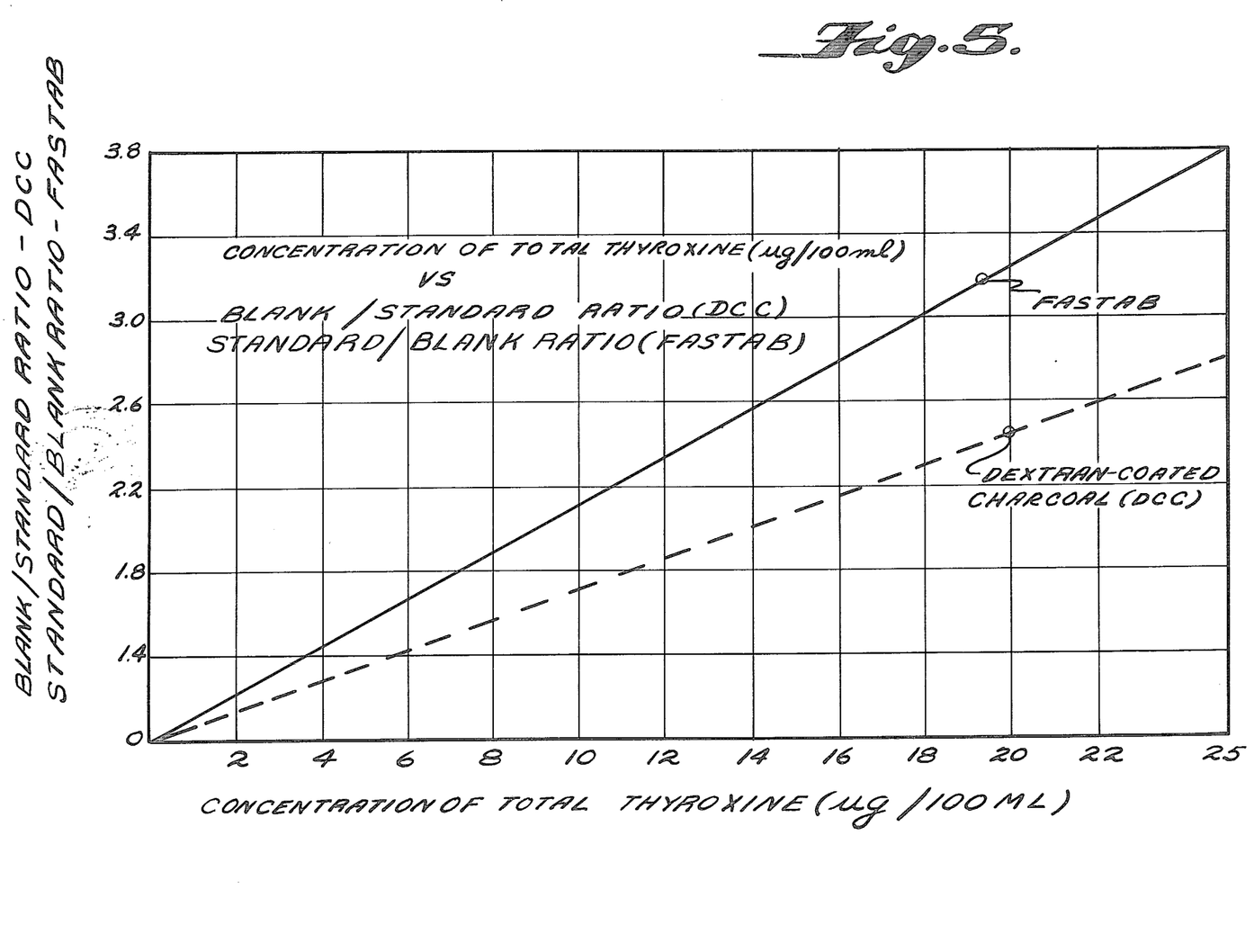
FIG. 5 is a graph showing a total thyroxine calibration curve comparing a conventional dextran coated activated carbon slurry with FASTAB.

FIG. 5 illustrates the application of FASTAB (as prepared in Example 1) to total thyroxine (T4) radioimmunoassay and compares the results to those obtained using dextran-coated charcoal as the separating medium. When illustrating the calibration curve for dextran-coated charcoal, the ordinate is a dimensionless number that represents the ratio of counts in the blank tube divided by the counts in the standard tube. In illustrating the calibration curve when FASTAB is used to separate the unbound antigen from the antibody-bound antigen, the ordinate represents the ratio of counts in the standard tube divided by the counts in the blank tube. The abscissa in both instances represents the concentration of total tyroxine in units of micrograms per deciliter.

The procedure used to develop these curves follows below.

SERUM EXTRACTION

1. Volumetrically transfer 1 ml of serum dropwise into 2 ml of ethanol contained in a centrifugable tube. Cap the tube to prevent evaporation.
2. Immediately mix for 30 seconds on a high-speed Vortex mixer.
3. Centrifuge the mixture until the precipitated protein has been firmly packed at the bottom of the tube (3000 rpm for 5 minutes).

ASSAY PROTOCOL

1. To a group of tubes add 1 ml of the $^{125}$I-Thyroxine solution.
2. To tubes marked "patient," add 25 microliters of the extracted (patient) serum. To tubes marked "blank" and "correction" add 25 microliters of phosphate buffer pH 7.6. To tubes marked "standard" add 25 microliters of the serum based calibration standards which have been alcohol extracted as described above. Run all samples in duplicate.
3. Add 100 microliters of the thyroxine antibody solution to all tubes marked "patient," "standard" and "blank." To tubes marked "correction," add 100 microliters of phosphate buffer pH 7.6.
4. Add one FASTAB to each tube. Make sure the FASTAB is seated on the bottom of the tube. In developing the curve for dextran-coated charcoal, this step is omitted.
5. Allow the solution to stand for at least 1 hour.

THE FOLLOWING STEPS APPLY ONLY TO THE FASTAB ANALYSIS

6. After the incubation period, discard the solution from the tube and retain the FASTAB. Rinse the FASTAB by filling the tube with water and then discard the rinse solution.
7. Count the FASTAB for 60 seconds. Make sure the FASTAB is seated on the bottom of the tube.
8. Calculate the standard/blank ratio. Plot the ratio of standard/blank vs. concentration on coordinate graph paper. Obtain patient values directly from the calibration curve by forming the ratio patient/blank and reading the corresponding concentration on the graph.

THE FOLLOWING STEPS APPLY ONLY TO THE DEXTRAN COATED CHARCOAL

6. Add 0.5 ml of a cold watery suspension of dextran coated charcoal to all tubes. Mix and allow to set for 5 minutes.
7. Centrifuge all tubes at high speed for 7 minutes. Decant the supernatant into counting tubes and count each tube for 60 seconds.
8. Calculate the blank/standard ratio. Plot the ratio of blank/standard vs. concentration on coordinate graph paper. Obtain patient values directly from the calibration curve by forming the ratio of blank/patient and reading the corresponding concentration on the graph.

The above reagents were prepared as followed:

1. Phosphate Buffer, pH 7.6: Dissolve 13.92 g of dibasic potassium phosphate, 2.76 g of monobasic sodium phosphate, and 8.76 g of sodium chloride in 900 ml of water. Adjust pH of the resulting solution to 7.6 with 0.1N HCl or NaOH. Dilute with deionized water to 1000 ml and mix well. The resulting solution is stable for 6 months at 4° C.
2. $^{125}$I-Thyroxine Abbott, TETRAMET®-125: A quantity of stock $^{125}$I-Thyroxine in polyethylene glycol (M.W. = 400) so that a concentration of 700 picograms/ml. is obtained. Use phosphate buffer, pH 7.6 to make the dilution. Store at 4° C.
3. Dextran-Coated Charcoal Suspension:
    a. Charcoal Suspension - Weigh 5 grams of Norit A neutral Charcoal (Fisher Scientific Co.) and suspend in 100 ml of phosphate buffer pH 7.6 (item 1 above).
    b. Dextran Solution - Dissolve 0.5 gram of Dextran 70T (Pharmacia Fine Chemicals) in 100 ml of phosphate buffer pH 7.6.
    c. Mix equal volumes of charcoal and dextran solutions. Shake for 10 seconds and store at 4° C.
4. Thyroxine Antibody Solution - Open a vial of antibody (Wien Lab) and add 10.2 ml of phosphate buffer, pH 7.6. Swirl to dissolve. Stable 4 weeks or more at 4° C.

EXAMPLE 3

Figure 6:
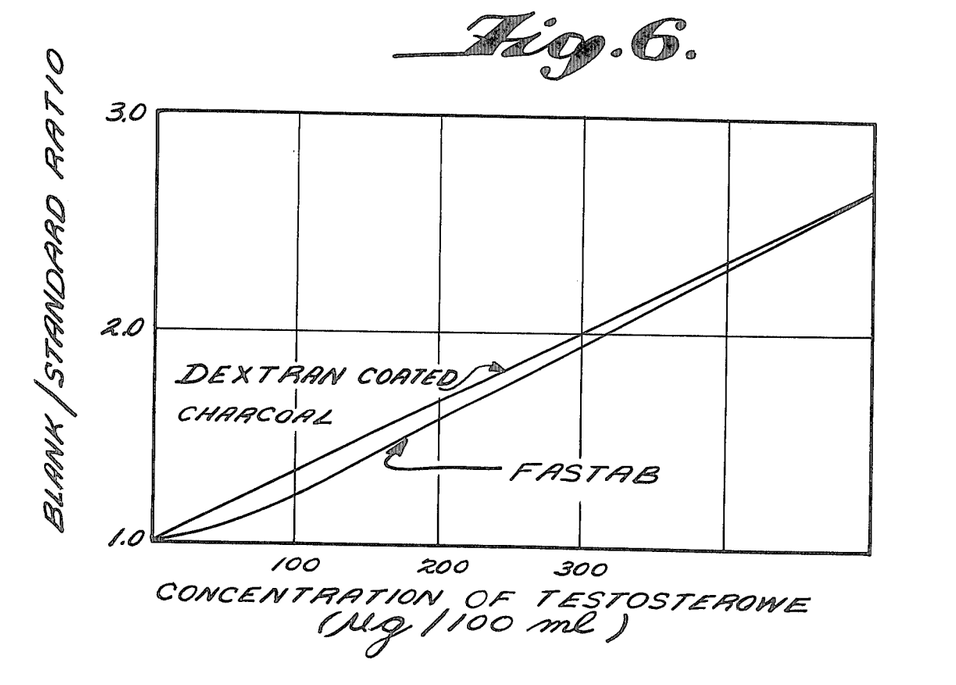
FIG. 6 is a graph showing a testosterone calibration curve.

FIG. 6 illustrates the application of FASTAB (prepared in Example 1) to the RIA of testosterone. The ordinate is the blank/standard ratio and the abscissa is the concentration of testosterone (ng/100ml) (ng is nanograms). The assay system is based on the general procedure outlined in Example 2 for iodinated samples but differs from it in the use of a scintillation cocktail necessary for the detection of tritium Labelled ($^3$H) samples.

A number of test tubes are set up containing the testosterone standards, 2 ml of phosphate buffer (pH 7.6), $^3$H - testosterone, 190 microliters ($\mu$l) of antiserum*, and one FASTAB. The tubes are incubated at 4° C. for 24 hours. At the end of the incubation period the supernatant is poured into a counting vial and 20 ml of the scintillation mixture is added. After 15 minutes the vial is counted. The resulting calibration curve is illustrated in FIG. 6 together with a calibration curve based on dextran coated carbon prepared as set out in Example 2 supra.

*Anti-testosterone

EXAMPLE 4

Figure 7:
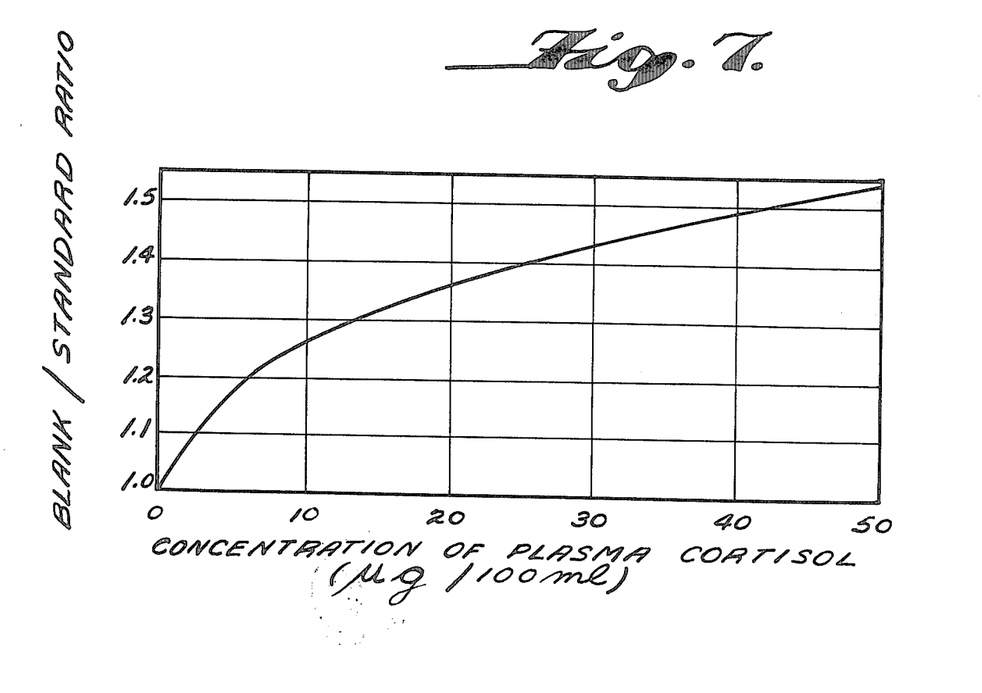
FIG. 7 is a graph showing a plasma cortisol calibration curve.

FIG. 7 illustrates the application of FASTAB (prepared in Example 1) to the RIA of plasma cortisol.

Tubes containing 0, 10, 20 and 40 μg per 100 ml of cortisol were set up. 1 ml of $^3$H-cortisol was added to each tube together with the antiserum* and one FASTAB. The mixture was allowed to incubate overnight at 4° C. after which time the supernatant was poured into a counting vial together with 10 ml of the scintillation liquid. The resulting calibration curve is illustrated in FIG. 7.

*Anti-cortisol

EXAMPLE 5

This Example illustrates the water-uptake of various hydrogels which are contemplated within the scope of invention.

Crosslinked 100% hydroxyethyl methacrylate/0.3% ethylene glycol methacrylate polymer has a water uptake of 60%. The water uptake values for other hydrogels are set forth in Tables 1 to 4 below. The "Diester" in the tables was ethylene glycol dimethacrylate and the amount is based on 100% of the other monomers.

EXAMPLE 6

The FASTAB was manufactured as follows using the indicated materials:

| | |
|---|---|
| MTGMA[(1)] | 30 grams |
| DM | 70 grams |
| Carbon (Darco S-51) | 10 grams in 90 cc water |
| Ethylene dimethacrylate | 1.0 gram |
| t-butyl hydroperoxide (TBPO) | As indicated |
| Ammonium persulfate | As indicated |
| Sodium metabisulfite | As indicated |

[(1)]MTGMA represents methoxytriglycol methacrylate

TABLE 1

Water Uptake Values of Hydrophilic Copolymers Based on Dimethyl-Acrylamide

| Water Uptake Percent | Dimethyl-acrylamide Percent | N-(hydroxypropyl)-Methacrylamide, Percent | Diester Percent |
|---|---|---|---|
| 200 | 31.7 | 67.3 | 0.3 |
| 400 | 50.0 | 50.0 | 0.3 |
| 600 | 60.0 | 40.0 | 0.3 |
| 800 | 68.3 | 31.7 | 0.3 |
| 1000 | 75.0 | 25.0 | 0.3 |

TABLE 2

| Water Uptake Percent | HEMA Percent | Dimethyl-acrylamide Percent | Diester Percent |
|---|---|---|---|
| 200 | 75 | 25 | 0.0 |
| 200 | 64 | 36 | 0.3 |
| 400 | 60 | 40 | 0.0 |
| 400 | 56 | 44 | 0.3 |
| 600 | 52 | 48 | 0.0 |
| 600 | 66 | 34 | 0.3 |
| 800 | 44 | 56 | 0.0 |
| 1000 | 25 | 75 | 0.0 |

TABLE 3

Water Uptake Values of Hydrophilic Copolymers Based on HEMA Methoxytriglycol Methacrylate

| Water Uptake Percent | HEMA Level[+] | Methoxytriglycol Methacrylate, Level[+] | Diester Level[+] |
|---|---|---|---|
| 100 | 61.7 | 38.3 | 0.3 |
| 100 | 55.0 | 45.0 | 1.0 |
| 200 | 41.6 | 58.4 | 0.3 |
| 200 | 30.0 | 70.0 | 1.0 |
| 300 | 33.0 | 67.0 | 0.3 |

TABLE 4

| Water Uptake Percent | HEMA Level[+] | Acrylamide Level[+] | Diester Level[+] |
|---|---|---|---|
| 100 | 85.0 | 15.0 | 0.3 |
| 200 | 62.4 | 37.6 | 0.3 |
| 300 | 50.0 | 50.0 | 0.3* |

*contains 10% water
[+]represents %.

The mold used was a pair of glass plates, inside dimensions 9.5 cm × 11.5 cm and separated by a gasket having a thickness of 2.3 mm.

1. Degas 15 g of the monomer mixture under vacuum for 2 hours.
2. Prepare a solution of 30 mg of ammonium persulfate in ½ cc water. Repeat for sodium metabisulfite.
3. Place the carbon containing water phase on a stirring plate and keep the solution well stirred.
4. To 10 g of the monomer mixture, add 30 mg of TBPO*, the solutions of ammonium persulfate and sodium metabisulfite, and 10 g of the water phase.

*TBPO represents t-butyl peroctoate

5. Rapidly aspirate the solution into a 50 cc syringe and then quickly inject it between the plates of the mold.
6. Place the mold in a 38° C. over for 2 hours.
7. Post-cure the mold, in a horizontal position, for 2 hours at 100° C.
8. Remove the molded sheet from the mold and rinse it in deionized water.
9. Place the molded sheet in water and allow it to swell to equilibrium at 4° C. (approximately 24 hours).

Using a cork borer, punch out discs from the hydrated molded sheet. The resulting discs measure approximately 10 mm in diameter by 4 mm thick and weigh approximately 250 mg. Store said disc in water at 4° C.

Figure 8:
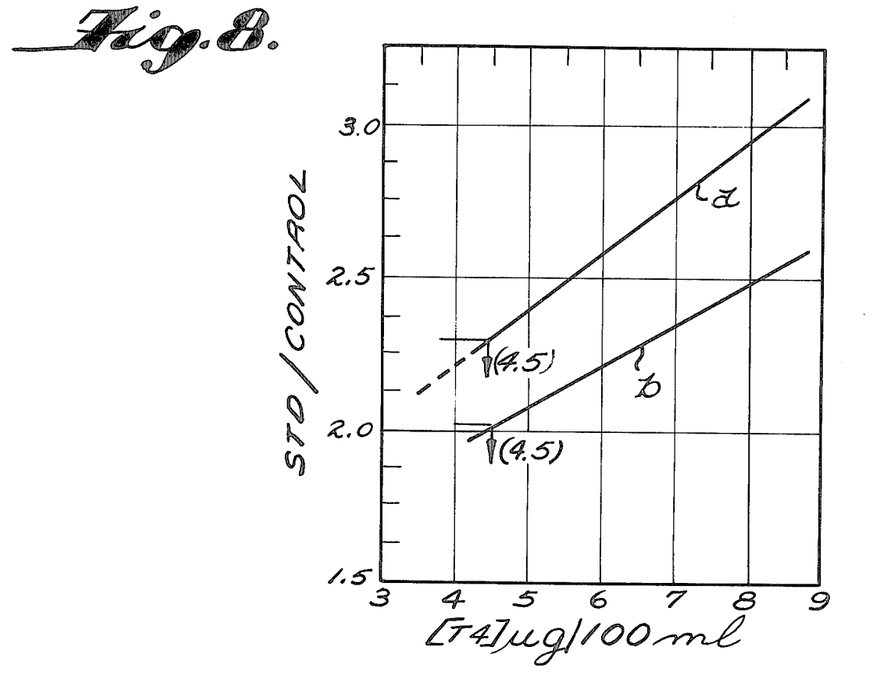
FIG. 8 is a graph based on a use of FASTAB under different conditions for making thyroxine calibration curves.

FIG. 8 demonstrates that by allowing FASTAB to reside in a solution of incubating antibody and antigen, the resulting values for patient serum unknowns are not materially effected. In one mode (b) the incubation was allowed to proceed in the absence of FASTAB for one hour. FASTAB was then added to separate bound from free antigen. In the second preferred mode (a), FASTAB is present in a solution of serum sample, tracer, and antibody for the duration of the incubation period. The resulting values for the patient serum unknown are identical in both instances (4.5 micrograms/100 ml).

EXAMPLE 7

Figure 9:
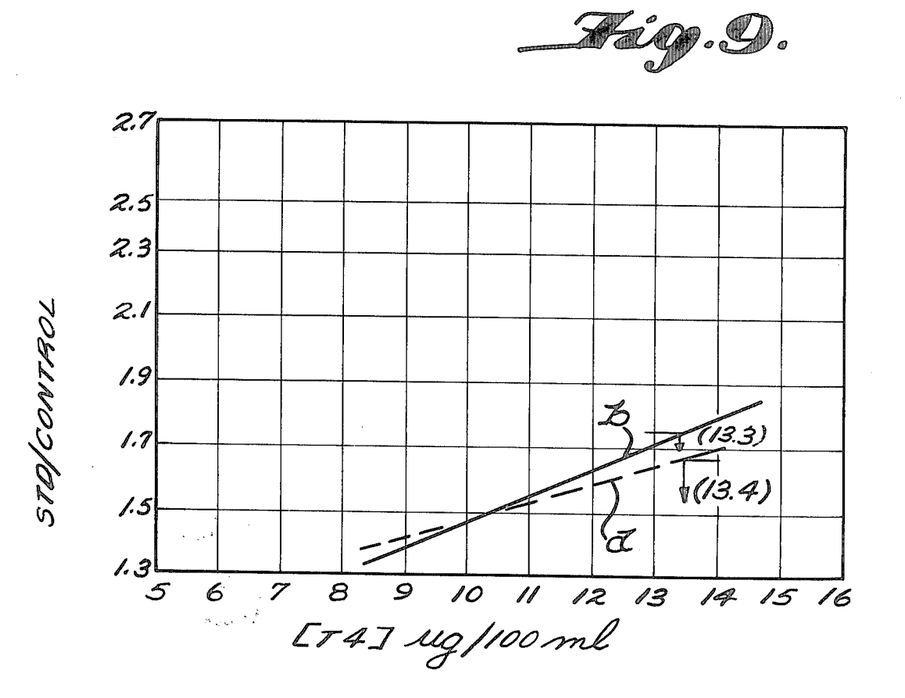
FIG. 9 is a graph comparing a dextran-coated carbon curve with FASTAB curves in determining thyroxine concentration.

Using the materials, method, and conditions of Example 6 supra, the curves shown in FIG. 9 were developed. These curves result from allowing FASTAB to reside in a solution of serum sample, tracer, and antibody for either 1 hour (a) or two hours (b). The resulting values for the patient serum unknown are clinically identical in both cases (13.3 and 13.4 micrograms/100 ml). Such clinical values reflect a relative lack of time sensitivity when using FASTAB to separate antibody-bound thyroxine from unbound thyroxine.

EXAMPLE 8

The invention is also useful in determining thyroid function directly by radioimmunoassay. The testing procedure determines the amount of serum thyroxine available for matabolic use. This quantity of thyroxine typically represents only ½ of 1% of the total thyroxine manufactured by the thyroid gland; the remaining 99½% is bound to serum constituents and is thus metabolically unavailable.

No single test has previously been successfully commercialized to directly assay the free thyroxine (F T4) concentration. Two tests must be run to make this same determination. The first test, known as the total serum thyroxine or T4 test, determines the total amount of thyroxine in serum, i.e., it makes no distinction between the free thyroxine component and the component which is bound to serum proteins. The second test, known as the T3 test, indicates the amount of thyroxine which has been bound to serum proteins. Both of these tests will together give an indication of the free thyroxine concentration. Thus the free T4 concentration can only be obtained by a roundabout method using reagents that are relatively expensive, namely (1) two types of antibody and (2) two types of readiolabelled molecules.

By using the novel hydrogel-sorbent articles, e.g., FASTAB, the free T4 determination can be directly assayed without the need for any antibody. FASTAB can discriminate between molecules on the basis of their size. FASTAB will readily absorb a low molecular weight species and exclude high molecular weight ones. FASTAB will absorb the free thyroxine molecule but will not absorb any thyroxine which has been bound to serum proteins.

The basic test for free T4 determination using FASTAB is accomplished by first adding a small but known amount of radioactive thyroxine to the serum sample and allowing it to reach an equilibrium with the serum proteins. The radioactive thyroxine which is not protein bound at equilibrium, exists in the same proportion as the free T4 already in the serum sample. This radioactive, free T4, component is then absorbed by the FASTAB and measured by an appropriate detector.

The entire test can be completed in about 1 hour. No antibody is required for this determination, the determination is made directly on the serum without the need to first extract the serum proteins by ethanol precipitation, and no centrifugation is necessary. The fact that the procedure requires no antibody or centrifugation represents a substantial savings in time and expense.

The procedure employed is as follows:
(1) There is obtained a serum sample and placing same in an appropriate test tube,
(2) Add a precise, known amount of radiolabeled thyroxine, e.g., labeled with $^{125}$I, (antigen),
(3) Add a FASTAB to the serum-antigen mixture,
(4) Allow the FASTAB to reside in said mixture for a specified period of time, e.g., 1 hour,
(5) Remove said FASTAB from the test tube, and
(6) Separately count both the test tube and the FASTAB in an appropriate gamma detector.

As indicated above, the articles of the invention can be in a wide variety of shapes, e.g., tablets, cylindrical, rectangular or hexagonal, rods, spheres, beads, cubes, coatings for tubes, or even in the form of tubes themselves, etc.

What is claimed is:

1. An article of manufacture comprising a hydrophilic polymer matrix and particulate microporous sorbent dispersed therein,
    A. said article being characterized by the following properties:
        (i) solid, (ii) insoluble in deionized water and lower alkanols, (iii) normally shape-retaining in the dehydrated state as well as in the fully hydrated state, (iv) water-swellable to the extent that is possesses a deionized water-uptake value of from 200% to 2200%, based on the weight of the dehydrated article, (v) a partition coefficient of at least 2, (vi) an average molecular weight diffusion limitation of about 10,000 Daltons, and (vii) a gross external surface area no greater than about one percent of the total surface area of total microporous sorbent dispersed therein;
    B. said polymer (i) having an average molecular weight greater than about 40,000, and (ii) a deionized water-uptake value in the range of from 60% to 4000%, based on the weight of said polymer; and
    C. the concentration of said sorbent being in the range of from 0.01 to 50 weight percent, based on the weight of said polymer.
2. The article of claim 1 wherein the concentration of said sorbent is in the range of from one to 30 weight percent, based on the weight of said polymer.
3. The article of claim 1 wherein said sorbent is characterized by: (i) pore volume of from 0.3 to 1.5 cc/gm, (ii) pore size of which at least 50 percent of the pores have a diameter of less than 1 micron, and (iii) surface area of from 5 square meters/gram to 4000 square meters/gram.
4. The article of manufacture of claim 2 wherein said sorbent is of the group consisting of alumina, activated carbon, ion exchange resins, silica and the molecular sieves.
5. The article of claim 4 wherein said hydrophilic polymer is a polymer of hydroxyalkyl 2-alkenoate, a polymer of hydroxy lower alkoxy lower alkyl 2-alkenoate, a partially hydrolyzed polymer of a vinyl ester of a carboxylic acid, a polymer of vinyl alkyl ether, a polymer of vinyl heterocyclics, a partially crosslinked polymer of alkylene oxide, or a polymer of alkenamide.
6. The article of manufacture of claim 1 in hydrated form.
7. The article of manufacture of claim 6 wherein the concentration of said sorbent is in the range of from one to 30 weight percent, based on the weight of said polymer.
8. The article of manufacture according to claim 7 wherein the hydrophilic polymer is a polymer of 2-hydroxyethyl methacrylate.
9. The article of manufacture according to claim 8 wherein the hydrophilic polymer is a polymer of 2-hydroxyethyl methacrylate and dimethylacrylamide.
10. The article of claim 7 in the form of a tablet, rod, sphere, or tube.
11. The article of claim 1 wherein the polymer is a polymer of a hydroxyalkyl alkenoate or a hydroxy lower alkoxy lower alkyl alkenoate.
12. The article of claim 11 wherein the sorbent is activated carbon, ion exchange resin, alumina, zirconium phosphate, hydrozirconium oxide, silica, or a molecular sieve.
13. The article according to claim 4 wherein the hydrophilic polymer is a polymer of the group consisting of hydroxy lower alkyl acrylate, hydroxy lower alkyl methacrylate, hydroxy lower alkoxy lower alkyl acrylate, hydroxy lower alkoxy lower alkyl methacrylate, vinylpyrrolidone, acrylamide, methacrylamide, N-lower alkylacrylamide, N-lower alkylmethacrylamide, N,N-di(lower alkyl)acrylamide, N,N-dilower alkylmethacrylamide, N-hydroxy lower alkylacrylamide, N-hydroxy lower alkylmethacrylamide and diacetone acrylamide.

14. The article according to claim 13 wherein the hydrophilic polymer is a polymer of hydroxy $C_2$–$C_3$ alkyl acrylate or methacrylate.

15. The article according to claim 14 wherein the sorbent is activated carbon.

16. The article according to claim 15 wherein said article has a gross external surface area no greater than about 0.01 percent of the total surface area of total microporous sorbent dispersed therein.

17. The article according to claim 16 in the form of a tablet, rod, sphere or a tube coated with the hydrogel.

* * * * *